United States Patent [19]
Batchelder et al.

[11] Patent Number: 5,510,894
[45] Date of Patent: Apr. 23, 1996

[54] SPECTROSCOPIC APPARATUS AND METHODS

[75] Inventors: David N. Batchelder, London; G. David Pitt, Gloucestershire, both of United Kingdom

[73] Assignee: Renishaw plc, Gloucestershire, United Kingdom

[21] Appl. No.: 351,175

[22] Filed: Nov. 30, 1994

Related U.S. Application Data

[63] Continuation of Ser. No. 13,063, Feb. 3, 1993, abandoned, and a continuation-in-part of Ser. No. 543,729, Aug. 16, 1990, Pat. No. 5,194,912.

[30] Foreign Application Priority Data

Jun. 8, 1991 [GB] United Kingdom ............... 9112343
Nov. 16, 1991 [GB] United Kingdom ............... 9124397

[51] Int. Cl.$^6$ ..................................................... G01F 3/34
[52] U.S. Cl. ............................................ 356/301; 356/326
[58] Field of Search ................................ 356/301, 326; 250/458.1, 459.1, 461.1, 461.2

[56] References Cited

U.S. PATENT DOCUMENTS

| | | | |
|---|---|---|---|
| 3,625,613 | 12/1971 | Abell et al. | 356/301 |
| 3,914,055 | 10/1975 | Wolga et al. | 356/301 |
| 3,999,854 | 12/1976 | Barrett . | |
| 4,030,827 | 6/1977 | Delhaye et al. . | |
| 4,081,215 | 3/1978 | Penney et al. . | |
| 4,397,556 | 8/1983 | Muller | 356/301 |
| 4,407,008 | 9/1983 | Schmidt et al. | 356/301 X |
| 4,586,819 | 5/1986 | Tochigi et al. | 356/301 |
| 4,648,714 | 3/1987 | Benner et al. | 356/301 |
| 4,649,557 | 3/1987 | Hornstra et al. | 378/84 |
| 4,942,299 | 7/1990 | Kazmerski | 250/306 |
| 5,091,652 | 2/1992 | Mathies et al. | 250/458.1 |
| 5,239,178 | 8/1993 | Derndinger et al. | 250/234 |

FOREIGN PATENT DOCUMENTS

| | | |
|---|---|---|
| 67319/90 | 5/1991 | Australia . |
| 0056426 | 5/1983 | European Pat. Off. . |
| 0380904 | 8/1990 | European Pat. Off. . |
| 0426571A1 | 5/1991 | European Pat. Off. . |
| 2596863 | 10/1987 | France . |
| 62-269048 | 11/1987 | Japan . |
| 1577198 | 10/1980 | United Kingdom . |
| WO88/07179 | 9/1988 | WIPO . |
| WO92/17806 | 10/1992 | WIPO . |

OTHER PUBLICATIONS

Flaugh et al., "Development of a New Optical Wavelength Rejection Filter: Demonstration of Its Utility in Raman Spectroscopy", Applied Spectroscopy, vol. 38, No. 6, Nov.–Dec. 1984, pp. 847–850.

Asher et al., "Crystalline Colloidal Bragg Diffraction Devices", Spectroscopy, vol. 1, No. 12, 1986, pp. 26–31.

Batchelder "Multichannel Raman Spectroscopy with a Cooled CCD Imaging Detector", ESN–European Spectroscopy News, 90, 1988, 28, 32, 34.

Delhaye et al. "Raman Microprobe and Microscope with Laser Excitation". Journal of Raman Spectroscopy, 3(1975) pp. 33–43.

Karger et al. "Laser Raman Spectrometer for Process Control", Applied Optics, vl. 12, No. 9, Sep. 1973, pp. 2083–2087.

(List continued on next page.)

Primary Examiner—Vincent P. McGraw
Assistant Examiner—K. P. Hantis
Attorney, Agent, or Firm—Oliff & Berridge

[57] ABSTRACT

A spot of a sample is illuminated by laser light. Raman scattered light is collimated in a parallel beam by a microscope objective, and analyzed by a dispersive or non-dispersive analyzer (such as a diffraction grating or filter). A lens then focuses the Raman scattered light onto a two-dimensional photodetector array in the form of a charge-coupled device (CCD). A confocal technique is described to eliminate light scattered from outside the focal plane of the objective. This may be done by binning together a few pixels of the CCD at the focal point of the lens, or by image processing techniques in a computer.

21 Claims, 4 Drawing Sheets

OTHER PUBLICATIONS

"Optical Determination of Crystal Axis Orientation in Silicon Fragments or Devices", IMB Technical Disclosure Bulletin, vol. 27, No. 7A, Dec. 1984.

Duncan et al. "Imaging Biological Compounds Using the Coherent Anti–Strokes Raman Scattering Microscope", Optical Engineering, vol. 24, No. 2, Apr. 1985, pp. 352–355.

Dhamelincourt, "Laser Molecular Microprobe", Source Unknown, pp. 48–53.

Photon scanning tunneling microscopy, R. C. Reddick et al., Review of Scientific Instruments 61 (1990) Dec., No. 12, New York, USA, pp. 2669–3677.

Scanning probe microscopy: Current status and future trends, H. Kumar, Journal of Vacuum Science & Technology A8 (1990) Jan./Feb., No. 1, New York, USA, pp. 363–367.

Studying single living cells and chromosomes by confocal Raman Microspectroscopy, G. J. Puppels et al., Nature, vol. 347, Sep. 20, 1990, pp. 301–303.

Mapping materials properties with Raman spectroscopy utilizing a 2–D detector, D. Kirk Veirs et al., Applied Optics, vol. 29, No. 33, Nov. 20, 1990, New York, USA, pp. 4969–4980.

Insight Brochure, Meridian Instruments, Inc. 4 pgs. copyrighted 1991.

Hadamard Transform Raman Imaging, Patrick J. Treado et al., Applied Spectroscopy, vol. 42, No. 5, 1988, pp. 897–900.

Hadamard Transform Raman Microscopy of Laser–Modified Graphite Electrodes, Patrick J. Treado et al., Applied Spectroscopy, vol. 44, No. 8, 1990, pp. 1270–1275.

Optical Sectioning Raman Microscopy, Anurag Govil et al., Applied Spectroscopy, vol. 45, No. 10, 1991, pp. 1604–1606.

"Scanning Multichannel Technique for Improved Spectrochemical Measurements with a CCD Camera and its Application to Raman Spectroscopy", V. Deckert et al., Applied Spectroscopy, vol. 46, No. 2, 1992, pp. 322–328.

SPECTROSCOPIC APPARATUS AND METHODS

CROSS-REFERENCES TO RELATED APPLICATIONS

This is a Continuation of application Ser. No. 08/013,063 filed Feb. 3, 1993, now abandoned, which in turn is a continuation-in-part of International Patent Application No. PCT/GB92/01026, filed 8th Jun., 1992, published under No. WO 92/22793. It is also a continuation-in-part of International Patent Application No. PCT/GB92/01025, filed 8th Jun., 1992, published under No. WO 92/22805. Furthermore, it is a continuation-in-part of U.S. patent application Ser. No. 07/543,729 filed 6th Aug., 1990, to be issued as U.S. Pat. No. 5,194,912, which is the U.S. national stage of International Patent Application No. PCT/GB89/01532, filed 22nd Dec., 1989, published under No. WO 90/07108.

BACKGROUND OF THE INVENTION

This invention relates to apparatus and methods in which spectroscopy is used to analyse a sample, for example making use of the Raman effect.

The Raman effect is a phenomenon in which a sample scatters incident light of a given frequency, into a frequency spectrum which has lines caused by interaction of the incident light with the molecules making up the sample. Different molecular species have different characteristic Raman spectra, and so the effect can be used to analyse the molecular species present.

Prior arrangements of Raman analysis apparatus have been described in a paper "Raman Microprobe and Microscope with Laser Excitation", M. Delhaye and P. Dhamelincourt, Journal of Raman Spectroscopy, 3 (1975), 33–43, and also in our earlier International Patent Specification WO 90/07108, of which this application is a continuation-in-part. A sample is irradiated with monochromatic light from a laser, and the scattered light is analysed in order to select a particular line of the resulting Raman spectrum. The analysis may be performed by a dispersive device such as a diffraction grating, e.g. in a monochromator, or it may be performed as described in WO 90/07108 using a non-dispersive tunable filter. WO 90/07108 also discloses that the resulting Raman scattered light may be focused onto a charge-coupled device (CCD), which is a two-dimensional photo-detector array.

Other spectroscopic techniques are also known in which a sample is irradiated with monochromatic or even polychromatic light, and the light scattered is analysed. Examples include fluorescence spectroscopy and infra-red spectroscopy. The present invention is also applicable to such techniques.

It is possible to use such techniques in a confocal manner, in order to analyse only light scattered from a certain plane in the sample. This involves passing the scattered light through a spatial filter, comprising a very small pinhole (typically 10 μm) at the focus of a lens system. Light scattered from the required plane is brought to a tight focus at the pinhole and passes through, whereas light from other planes is not so tightly focused and is blocked. However, such a spatial filter is difficult to set up correctly, because of the need for careful alignment of the optical components to ensure tight focusing of the scattered light on the very small pinhole. For the same reason, it is difficult to maintain the optical components correctly in alignment after the initial setting up, and the system is also susceptible to vibration. The alignment is particularly difficult to perform in systems where only very low levels of scattered light are available for analysis, such as Raman systems, since it is then impossible to see the focused light.

SUMMARY OF THE INVENTION

One aspect of the present invention provides a spectroscopy method comprising:

illuminating a sample, to obtain therefrom a spectrum of scattered light;

analysing said spectrum;

passing at least one component of the analysed spectrum to a photodetector, light scattered from a given plane in the sample being focused on the photodetector while light scattered from other planes in the sample is not in focus on the photodetector; and detecting light which is in focus on the photodetector, thereby reducing the effect of light scattered from said other planes in the sample.

Another aspect of the invention relates to methods in which spectroscopic analysis of a sample is combined with measurements of the topography of the sample.

The invention also provides apparatus for performing these methods.

DESCRIPTION OF PREFERRED EMBODIMENTS

Figure 1:
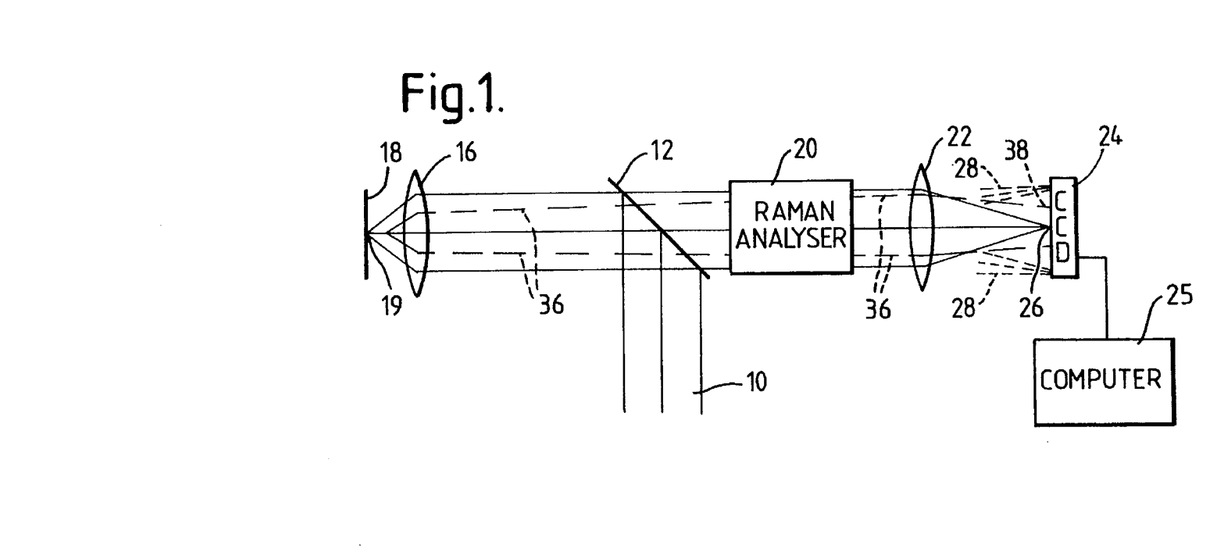
FIG. 1 is a schematic diagram of a first embodiment of Raman analysis apparatus.

The first embodiment of the apparatus illustrated in FIG. 1 is based upon the apparatus shown in WO 90/07108 and corresponding U.S. patent application Ser. No. 07/543,729 which issued as U.S. Pat. No. 5,194,912 on Mar. 16, 1993, which are incorporated herein by reference and to which the reader should refer for further details. An input laser beam 10 is reflected through 90° by a dichroic filter 12, placed at 45° to the optical path. The laser beam then passes to a microscope objective lens 16, which focuses it to a spot at its focal point 19 on a sample 18. Light is scattered by the sample at this illuminated spot, and is collected by the microscope objective lens 16 and collimated into a parallel beam which passes back to the dichroic filter 12. The filter 12 rejects Rayleigh scattered light having the same frequency as the input laser beam 10, and transmits the Raman scattered light. The Raman scattered light then passes to a Raman analyser 20.

The Raman analyser 20 may comprise one or more tunable non-dispersive filters for selecting a Raman line of interest, as disclosed in WO 90/07108, e.g. a dielectric interference filter which can be tilted to a desired angle relative to the optical axis in order to tune it. Alternatively, it may comprise a dispersive element such as a diffraction grating, either in a conventional monochromator arrangement or in the arrangement described in our copending U.S. patent application Ser. No. 07/976,513. In either case, the light from the analyser 20 is focused by a lens 22 onto a suitable photo-detector. A two-dimensional photo-detector array is preferred. In the present embodiment a charge-coupled device (CCD) 24 is used, which consists of a two-dimensional array of pixels, and which is connected to a computer 25 which acquires data from each of the pixels and analyses it as required. Where the Raman analyser 20 comprises a tunable non-dispersive filter, light of the selected Raman frequency is focused at 26 on the CCD 24. Where a dispersive element such as a diffraction grating is used, the analyser 20 produces not a single spot but a spectrum having various bands as indicated by broken lines 28, spread out in a line along the CCD 24.

The sample 18 may be mounted on an X-Y table so that the focal point 19 can be scanned across it in X and Y directions, e.g. under control of the computer. The focal point 19 may also be adjustable in the depth direction, either by movement of the sample 18 or of the lens 16 along the optical axis. Again, this may be under the control of the computer 25.

Figure 2:
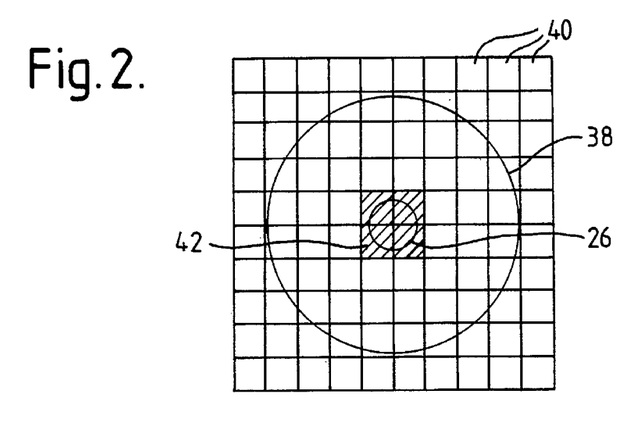
FIGS. 2 and 3 are schematic plan views of parts of a CCD when used with the apparatus of FIG. 1.

Light from the focal point 19 of the lens 16 is brought to a tight focus at 26 on the CCD. However, as illustrated by the broken lines 36, light from in front of or behind the focal point 19 is brought to a more diffuse focus. In the case where a non-dispersive filter is used for the analyser 20, the effect is illustrated in FIG. 2 which is a plan view of part of the CCD 24. Individual pixels of the CCD are shown as squares 40. The pixels may typically have a pitch of 22 μm or less. A circle 26 represents the distribution of light scattered from the focal point 19, while a circle 38 represents the more diffuse focus of light scattered from elsewhere in the sample. When analysing data, the computer 25 bins together a few pixels 42, shown shaded, which receive the light focused at 26. Extraneous light from elsewhere within the circle 38 is ignored by the computer. This is readily achieved by computer software which reads the data from each pixel 40 serially, in turn, adding together the data from the pixels 42 and ignoring the rest.

The combination of the CCD with the computer thus gives the same effect as the pinhole in a conventional spatial filter. If the lens 16 is focused on the surface of the sample, it is possible to filter out light scattered from behind the surface within the sample, so that analysis of the surface itself may be carried out. Alternatively, it is possible to deliberately focus the lens 16 to a point within the sample, thereby filtering out light scattered from the surface. Thus confocal behaviour has been achieved without the use of an extra spatial filter.

Figure 3:
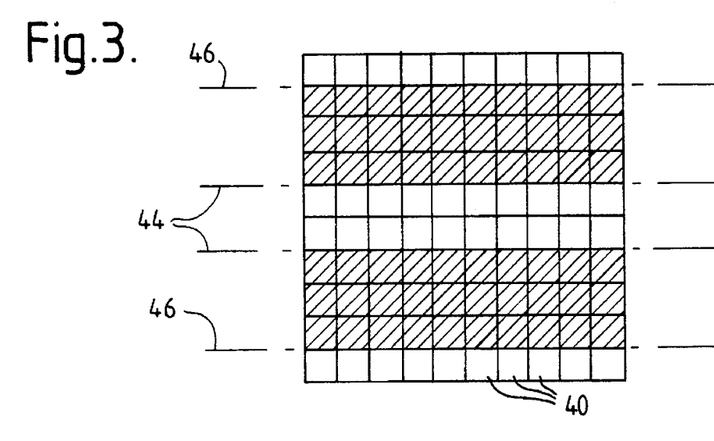

When a diffraction grating or other dispersive element is used as the analyser 20 in FIG. 1, and it is desired to view a full Raman spectrum rather than just a single Raman band, full confocal spectroscopy is not possible with such simple software. Partial confocal behaviour can be achieved, however, by operating the CCD 24 and computer 25 as indicated in FIG. 3. The diffraction grating disperses the Raman spectrum from the sample across the CCD in a line. The width of the line is smallest for light which has been scattered from the focal point 19, for example in the unshaded region between the lines 44 on the CCD in FIG. 3. Light from planes outside the focal plane which contains the focal point 19 would be scattered into a broader line, such as defined between the lines 46 in FIG. 3. To obtain partial confocal behaviour, therefore, the computer 25 is programmed (in a similar manner to that described above) to capture data only from those pixels of the CCD lying in the region between the lines 44, and excluding light received elsewhere on the CCD. This excludes light received in the shaded region of FIG. 3 from outside the focal point 19.

The reason that the arrangement of FIG. 3 exhibits only partial confocal behaviour is because the spatial filtering provided by the CCD and computer occurs only in one dimension and not two. This can be overcome by using the embodiment of FIG. 4, consisting of the same elements as found in FIG. 1, with the addition of a spatial filter 14. The same reference numbers have been used as in FIG. 1.

Figure 4:
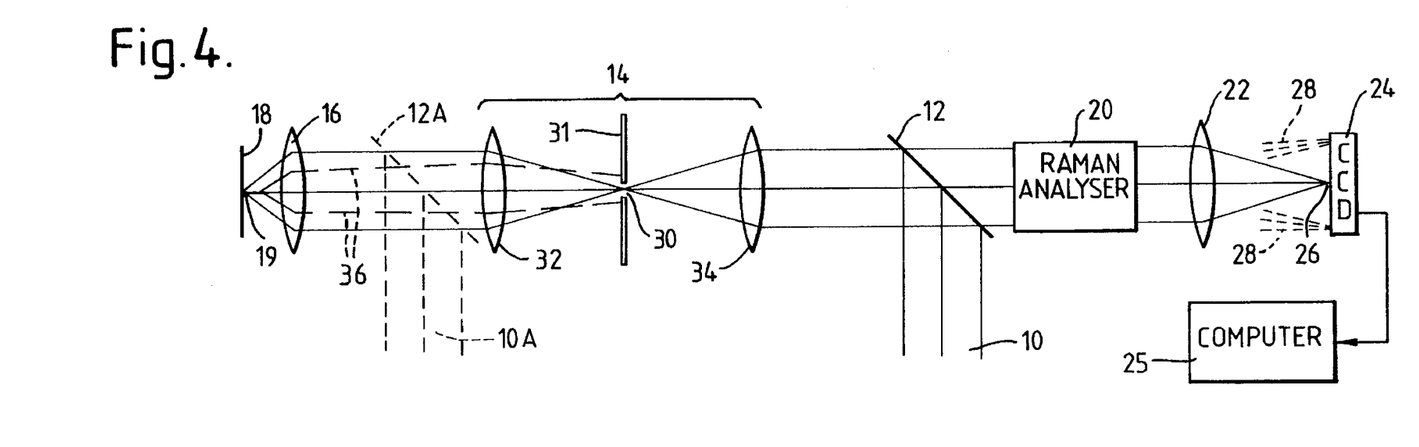
FIG. 4 is a schematic diagram of further embodiments of Raman analysis apparatus.

The spatial filter 14 comprises two lenses 32,34, and a screen 31 having a slit 30, extending normal to the plane of the paper. The lens 32 focuses the parallel beam of scattered light down to a very tight focus which passes through the slit 30, and the lens 34 collimates the light back into a parallel beam. The input laser beam 10 is likewise focused down to a very small spot to pass through the slit 30. The effect of the slit 30 is that the microscope objective 16 acts confocally. That is, substantially only the light scattered at the focal point 19 of the lens 16 passes through the slit 30. As indicated by broken lines 36, light which is scattered in front of or behind the focal point 19 is not brought to a focus at the aperture 30, and is therefore substantially blocked by the screen 31.

Figure 5:
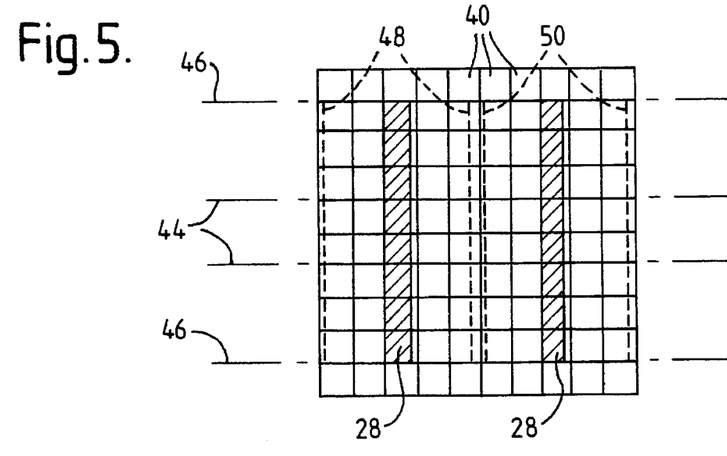
FIG. 5 is a schematic plan view of part of a CCD when used with the embodiment in FIG. 4, FIGS. 6 and 7 are plan views of a CCD, used for explaining another embodiment of Raman analysis apparatus.

FIG. 5 is a plan view, corresponding to FIGS. 2 and 3, of the CCD when used with the embodiment of FIG. 4. Light passing through the slit 30 is dispersed by the diffraction grating analyser 20 into individual bands 28 of the Raman spectrum. Without the slit 30, light corresponding to the bands 28, but scattered from outside the focal point 19, would appear in broader regions lying between the pairs of broken lines 48,50. It will be appreciated that the slit 30 provides only one-dimensional spatial filtering, such that each of the Raman bands 28 has been spatially filtered in the horizontal direction of FIG. 5. However, some light from outside the focal point 19 can still pass through the slit 30 and be received in the area of FIG. 5 which corresponds to the shaded regions of FIG. 3. To overcome this, the computer 25 is programmed as in the FIG. 3 embodiment, to process only data from the pixels lying between the lines 44 and to exclude the other pixels lying between the lines 46. This provides spatial filtering in the vertical direction, and together with the horizontal spatial filtering provided by the slit 30, full two-dimensional confocal behaviour is achieved.

An advantage of this arrangement over an arrangement in which a pinhole is used instead of the slit 30, is that it is much easier to align a slit than a pinhole.

If desired, it is possible to provide the dichroic filter in the position indicated in broken lines at 12A in FIG. 4, instead of in the position indicated at 12. The laser beam then enters the system at 10A, instead of 10. This arrangement has the advantage that the input laser beam does not have to pass through the spatial filter 14. Consequently, there is no risk of the laser beam hitting the edges of the aperture 30 and causing scattering from there. Such scattering would be undesirable, since unless the edges of the aperture are kept extremely clean, any dirt will cause unknown Raman scattered light to pass through the analyser 20 and be registered on the CCD 24. Conversely, however, arranging the dichroic filter at the position 12 has the advantage that the easily visible laser light can be used to adjust the positioning the aperture 30 when setting the apparatus up. With the dichroic filter at 12A, the Raman scattered light passing through the dichroic filter to the spatial filter 14 is insufficient to be visible. Furthermore, placing the dichroic filter at 12 means that the spatial filter 14 can easily be added to the existing apparatus as described in WO 90/07108, between the microscope and the remainder of the apparatus, and is easily accessible for adjustment.

In order to act as a spatial filter, the width of the slit 30 should be very small, typically 10 µm or even less. A maximum width might be 50 µm. Thus, the slit 30 should not be confused with the entrance and exit slits commonly provided in conventional monochromators which are much larger, say 200 µm at the least, in order to collect an adequate amount of light. A wider slit can however be used if lesser confocal action can be tolerated.

The various examples of the invention described above have used a CCD as the detector. However, to detect light in the circle 26 in FIG. 2, while rejecting light outside this circle, it is possible to use a single photo-detector of the correct size, e.g. an avalanche photodiode. This arrangement can also be used to detect a single Raman band produced by a diffraction grating. To detect the light between the lines 44 in FIGS. 3 and 5, while rejecting other light, it is possible to use a one-dimensional (i.e. linear) photo-detector array having an appropriate width.

A further possibility is to use those pixels of the CCD which are not otherwise used (e.g. those outside the circle 38 (FIG. 2) or outside the lines 46 (FIGS. 3 and 5)) to detect the DC level of background light. This can then be subtracted by the computer 25 from the signals produced by the pixels of interest.

Figure 6:
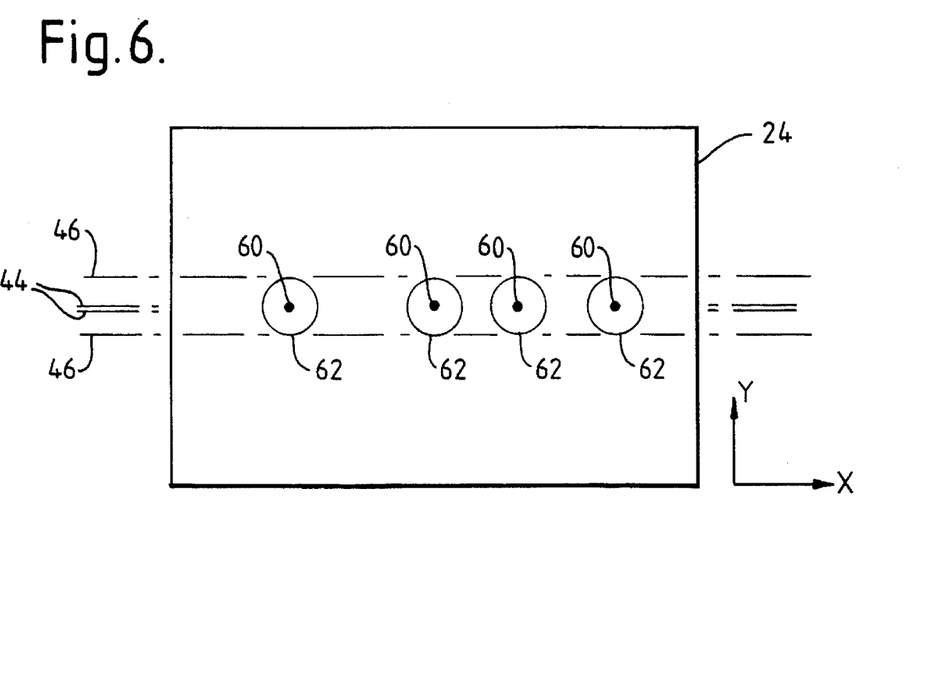
Figure 7:
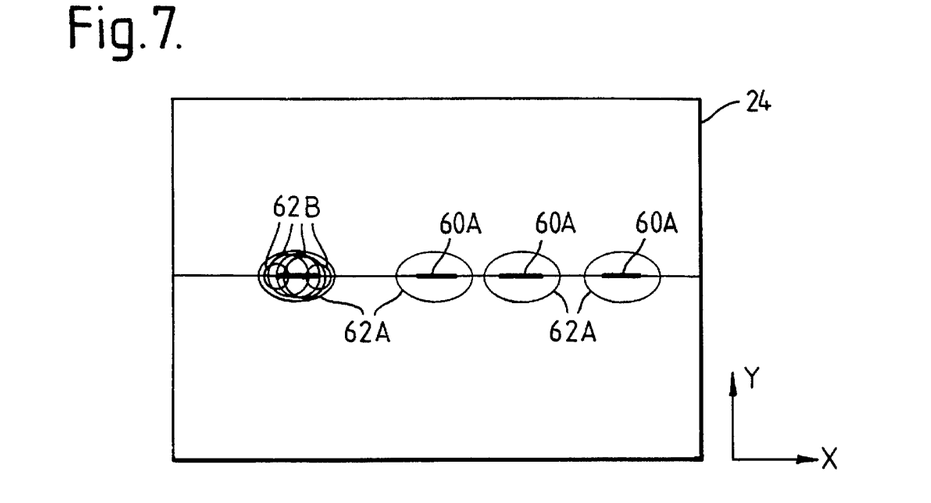

FIGS. 4 and 5 above have illustrated how full confocal behaviour can be obtained when a dispersive device such as a diffraction grating is used as the analyser 20. FIGS. 6 and 7 will now be used to describe techniques in which similar results are achieved, but without the need for the spatial filter 14 (that is, using hardware as shown in FIG. 1). These techniques involve the use of more sophisticated image processing software within the computer 25, to analyse the data received from the CCD 24. Compared with the embodiment of FIGS. 4 and 5, therefore, these techniques have the advantage of a simpler and cheaper opto-mechanical arrangement, at the expense of computer processing which is more time consuming and which may require a larger computer.

FIG. 6 is a view of the CCD 24 corresponding to FIG. 3, but showing more detail. The bands of the Raman spectrum produced by the dispersive analyser 20 (in an idealised case) are indicated by the small spots 60, lying within the lines 44. Such an idealised picture would only be obtained, however, if the following three assumptions were valid:

(a) the illumination of the sample 18 would need to be point-like, rather than illumination over a small area;

(b) all scattering would have to be from the focal plane of the lens 16, and not from adjacent planes above or below the focal point; and (c) the Raman scattering would need to be caused by the interaction of photons with phonons having a very precisely defined frequency value, so that each Raman band is sharp and has a very narrow width (i.e. a precisely defined wave number).

In real life, of course, these assumptions cannot be completely satisfied. The result of non-satisfaction of assumptions (a) and (b) will be a blurring of the image, as indicated by the larger circles 62 in FIG. 6, within the lines 46. The effect of not having a precisely defined phonon frequency (assumption (c)) is to broaden each of the Raman bands, giving the lines 60A shown in FIG. 7 in place of the spots 60 shown in FIG. 6. Correspondingly, the blurring is now as shown by the ellipses 62A, instead of the circles 62. The purpose of confocal techniques such as in the preferred embodiments of the present invention is to reduce the blurring effect particularly where assumption (b) is not satisfied.

The image processing algorithms which may be performed by software in the computer 25 have the effect of reducing or removing the blurring, to recover the spots 60 from the circles 62, or to recover the lines 60A from the ellipses 62A. In either case, the first step of the algorithm is to read all the data of the image from the CCD into the memory of the computer 25 (or into a suitable storage medium such as a hard disk). The data is stored within the computer in an array, having one storage location corresponding to each pixel of the CCD.

The next step of the algorithm is to scan the stored data in a direction corresponding to the direction X shown in FIGS. 6 and 7. This may be performed along a row of the stored array of data corresponding to one row of pixels within the lines 44. From this scan, the algorithm determines the point of maximum illumination in the middle of each circle 62. In a simple case, in which the circles 62 are assumed to be truly circular, and no information is required about the width of each individual Raman band, the algorithm can now output the position of each point of maximum illumination, in terms of the wave number of the corresponding Raman band. In this simple case, the algorithm can then (for each of the circles 62) determine the sum (or the average) of the values of the illumination which have just been scanned within that circle 62. This value is also output, to give an intensity value associated with each Raman band.

A more complicated algorithm may scan all the pixels between the lines 46 (i.e. a two-dimensional scan instead of the previous one-dimensional scan). For each of the circles 62, this algorithm then determines the centroid, and outputs the position of that centroid in the X direction, in terms of the wave number of the corresponding Raman band. Again, the intensity of this Raman band may be determined by summing or averaging the values just scanned within the circle 62 concerned.

However, neither of the above two algorithms give information about the width of the Raman band, as indicated by the lines 60A in FIG. 7. Neither do they give information about the shape of the Raman band (i.e. the intensity distribution within the line 60A). More sophisticated image processing techniques may be utilised if such information is required. For this, the software may perform an algorithm as follows. This algorithm is based upon the assumption that the ellipse 62A may be considered as a number of imaginary, overlapping circles 62B, each imaginary circle being centred upon a different pixel within the line 60A, and each imaginary circle corresponding to the blurring (produced in the same way as in a circle 62 in FIG. 6).

This algorithm proceeds as follows. Firstly, the data for an ellipse 62A is scanned as previously, to determine the centroid or point of maximum illumination of the ellipse. Next, the data for a column of pixels which includes this point is scanned in the Y direction, to determine the intensity distribution at various different radii from this centre point. As an approximation, it may be assumed that this intensity distribution corresponds to that of the imaginary circle which is centred on the pixel at the centroid of the ellipse, and that this imaginary circle has the same distribution in the X direction. However, the distribution as measured in the X direction will not correspond, since this measured distribution will also include contributions from all the other imaginary circles.

The next step of the algorithm, therefore, is to repeat this scan in the Y direction, for each of the other imaginary circles. That is, a Y distribution is determined corresponding to each pixel along the line 60A. To obtain a true intensity value for a given pixel in the line 60A, the algorithm next subtracts from the measured intensity value of that given pixel the contributions from all the other imaginary circles. For each of the imaginary circles, the value to be subtracted is the intensity value for the appropriate radius within that circle, determined from the Y distribution scan corresponding to that circle. The appropriate radius to use corresponds to the distance between the pixel under consideration and the centre of the circle concerned. Such a subtraction takes place for each of the imaginary circles. The whole process is repeated for every pixel along the line 60A.

The final step of this algorithm is to output the resulting intensity value for each pixel within the line 60A, along with the corresponding wave number (position in the X direction).

It is of course possible to devise even more sophisticated image processing algorithms if desired. For instance, algorithms may be devised to process blurring which is more complex than indicated by the circles 62 or ellipses 62A. Examples include cases where the illuminated area 19 of the sample 18 has a non-uniform surface roughness, or has a faceted surface (e.g. diamond film). Another example is where a substantial area of the sample is illuminated by the laser light (e.g. by having a slightly convergent or divergent incoming laser beam 10) and a non-dispersive filter is used for the Raman analyser 20, in order to focus a two-dimensional image of the illuminated area on the CCD. Deconvolution techniques can be used to process the resulting image data.

The methods described above may be used in an analogous fashion for other spectroscopic techniques than Raman spectroscopy, e.g. fluorescence spectroscopy and infra-red spectroscopy.

We will now describe apparatus and methods in which spectroscopy techniques are used in conjunction with techniques for analysing the surface topography or surface profile of a sample. Such techniques are also described in International Patent Specification No. WO 92/22805, of which this application is a continuation-in-part, and which is incorporated herein by reference.

Figure 8:
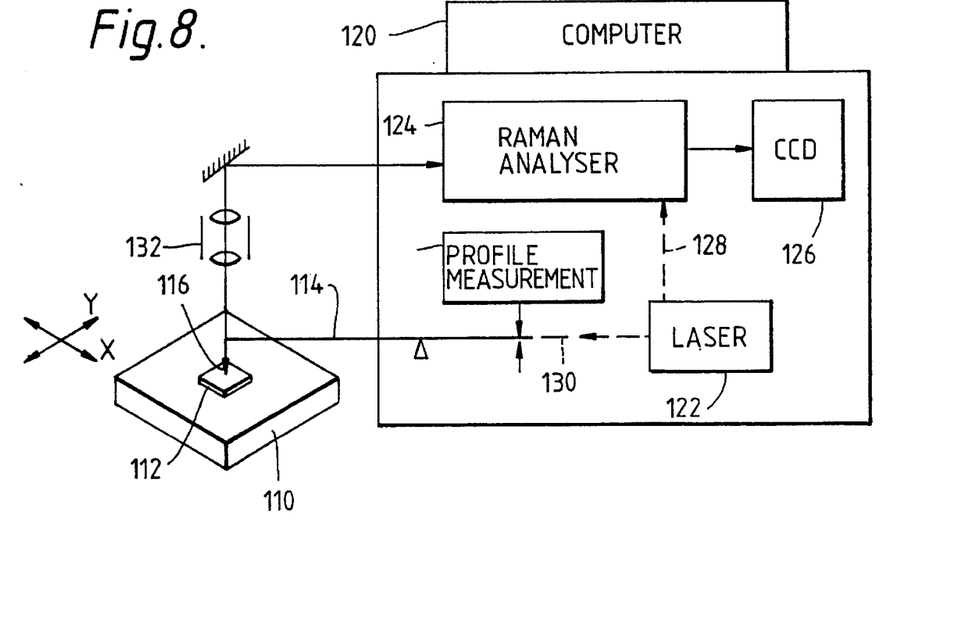
FIG. 8 is a schematic representation of a still further embodiment.

Referring firstly to FIG. 8, the apparatus includes a table or stage 110, upon which a sample 112 to be analysed can be mounted. The table 110 is provided with precision drives and precision measurement transducers, in a well known manner, so that it can be moved in the two horizontal directions X and Y. The free end 116 of a fine needle 114 rests on the surface of the sample 112, and traverses the sample surface as the table 110 is moved. The tip 116 of the needle 114 is extremely fine, so that the needle 114 is caused to move in response to microscopic variations in the profile of the surface of the sample 112. These movements of the needle 114 are picked up by a profile measurement device 118. This device 118 and the X,Y movement of the table 110, are controlled by a computer 120, as the tip 116 scans an area of the surface of the sample 112, so as to build up a picture of the height profile of the surface at every point within the area. The arrangement so far described uses well known techniques such as found in the surface profile measurement devices sold under the Trade Mark TALYSURF by Rank Taylor Hobson Ltd., P.O. Box 36, New Star Road, Leicester, LE4 7JQ, England.

This surface profile measurement is combined with Raman analysis apparatus generally of the type described in WO90/07108, to which reference should be made for further details. Briefly, light from a laser 122 is directed onto the surface of the sample 112, in a manner described more fully below. Raman scattering occurs, depending upon the molecular species present in the sample surface, and the resulting Raman spectrum is taken to a Raman analyser 124, again in a manner described below. The analyser 124, which is desirably also controlled by the computer 120, contains filters and other optical components as described in WO90/07108. The analyser 124 may be used in any of the ways described in that specification, including tuning a tunable filter thereof so as to select a line of the Raman spectrum which is characteristic of a molecular species of interest in the sample 112. Alternatively, the tunable filter of that specification may be replaced by a fixed filter, which selects just one desired Raman line. This makes a simpler, cheaper apparatus which is dedicated to the analysis of a specific molecular species, e.g. for use in a specific application. The Raman analyser 124 may be used in either the microscope or microprobe modes as described in that specification. Either way, the output beam of the analyser is taken to a suitable detector, such as a charge coupled device (CCD) 126 which produces a two-dimensional video image of the sample. This image can be analysed pixel by pixel in the computer 120. If used in the microprobe mode, the tunable filter may be replaced by a diffraction grating, allowing several lines of the Raman spectrum to be dispersed across the CCD 126.

If it is desired to use the Raman analyser in the microscope mode, illuminating a relatively large area of the surface of the sample 112 and forming a two-dimensional image thereof on the CCD 126, then the illuminating light from the laser 122 is fed via the Raman analyser 124, as indicated by broken line 128, and through a microscope objective lens system 132 to the sample. This is the same arrangement as shown in WO90/07108. The two-dimensional image of the surface of the sample 112 is focused onto the CCD 126 through the microscope objective 132. The needle tip 116 of the surface profile measurement device will be visible in this two-dimensional image. This enables the computer 120 to correlate the position of the surface profile measurement derived by the device 118 at any given instant with the position in the two-dimensional image produced by the Raman apparatus. Alternatively, since the X,Y positions of the microscope objective 132 and the needle tip 116 are fixed relative to each other, the position of the needle tip 116 relative to the CCD 126 may be determined only once and then stored in the computer 120 for use in the future correlation of the positions of profile measurements relative to the CCD image. In this way, the computer 120 builds up a two-dimensional picture which gives information about microscopic surface profile (height) variations, correlated with information about the variations in composition of the sample surface from place to place. In many samples, of course, the two will be closely related.

It is also possible, if desired, to construct the Raman analyser 124 in such a way that the Raman filter is removable. This enables a conventional image to be formed on the CCD 126 using the normal Rayleigh scattered laser light (or even ambient visible light) scattered from the sample surface. This further facilitates correlation of the position of the surface profile measurement at any given point.

Figure 9:
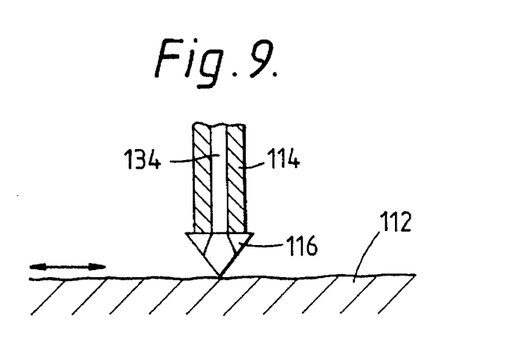
FIG. 9 is an enlarged vertical cross-sectional detail of part of the apparatus of FIG. 8.

Particularly when the Raman analyser is to be used in microprobe mode, instead of microscope mode, the incident light from the laser 122 may be fed to the sample 112 as indicated by the broken line 130, instead of the broken line 128. In this case, the needle 114 comprises an optical fibre, having a light transmitting core 134 as seen in FIG. 9. Thus, the incident light from the laser is fed along the needle 114 itself to the surface of the sample 112. The tip 116 of the needle 114 is made from glass, and is so designed as to bring the incident light travelling along the core 134 to a focus on the surface of the sample 112, at or very near to the point of contact between the tip 116 and the sample surface. The microscope objective 132 is focused onto the spot of light thus produced on the sample surface, to receive the scattered light from it, and pass it to the Raman analyser 124 as described above.

Figure 10:
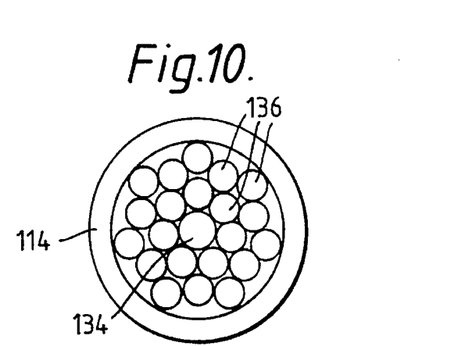
FIG. 10 is a horizontal cross-section of a modification of FIG. 9.

As an alternative to the use of the microscope objective 132, the needle 114 may comprise not just a single optical fibre core 134, but multiple cores as illustrated in cross-section FIG. 10. Here, a single central core 134 feeds the incident laser light to the sample, as in FIG. 9. The remaining cores 136 pick up a two-dimensional image of the spot formed on the surface of the sample, which is then taken directly to the Raman analyser 124. This enables microscopic Raman examination of the surface of the sample 112. Alternatively, there may be just one core 134 for incident light, and one core 136 for return light (or several cores 136 used in parallel) so that the Raman analyser can be used in microprobe mode only.

Figure 11:
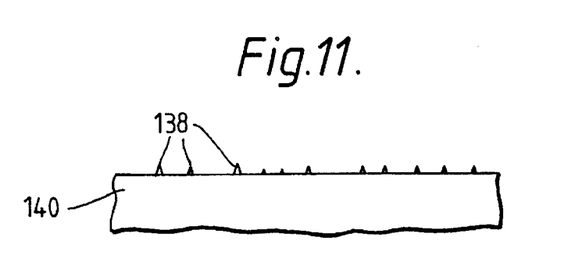
FIG. 11 is an enlarged elevation of a sample which can be analysed using the apparatus.

The apparatus described so far has many uses. One particular use illustrated in FIG. 11 is for quality assurance of diamond coatings, e.g. on cutting tools or abrasive materials, in which industrial diamonds 138 are embedded in a substrate 140, e.g. of nickel. To assess the quality of the surface, it is desirable to be able to measure surface profile, for example so as to determine grit size of the diamonds 138 and their distribution. An X-Y scan, with the sample placed on the X-Y table 110, determines such surface profile, using the profile measurement device 114,118. However, by itself this does not determine whether any particular height irregularity is a diamond particle or some other surface irregularity. Therefore, the Raman analyser 124 is used with a Raman filter tuned to the distinctive Raman line at 1332 cm$^{-1}$, characteristic of diamond. A two-dimensional image is therefore formed on the CCD 126, showing those areas of the sample surface which comprise diamond and those which do not. This can be correlated by the computer 124 with the profile measurements, for example to produce a two-dimensional image showing the profile only of diamond areas of the sample and ignoring irregularities in the substrate. The computer can also calculate the grit size of the diamond areas and the ratio of their distribution to non-diamond substrate areas. Such quality assurance can for example be undertaken after polishing of the surface of the sample, to determine how much diamond has been exposed by the polishing and whether a flat surface has been achieved. Flatness of the surface, for example, can be of importance if the sample is intended as a heat sink, in which a flat area largely consisting of diamond is required for heat-conducting purposes. The same is true if the sample is intended as a bearing surface.

The above description has used a mechanical profile measurement device 114,118. However, if desired, the surface profile may be determined optically, without the need for a mechanical needle 114.

In one optical technique, the microscope objective 132 is used to focus a small spot, e.g. of sub-micron size, on the surface of the sample, and Raman microprobe analysis is performed as above using this spot, in order to analyse any desired molecular species present at the point of the spot on the sample surface. The relative height of that particular point compared to other points on the sample surface is determined by triangulation techniques, in well known manner, using an off-axis detector. An example of such triangulation techniques is given in U.S. Pat. No. 4,851,843, incorporated herein by reference. An area of the sample 112 is analysed by X-Y scanning using the table 110. For each point on the surface of the sample during such a scan, the computer 120 receives both a height measurement from the triangulation device, and desired information from the Raman analyser and CCD. This is built up into a two-dimensional image, or otherwise analysed as desired in the computer 120.

Another optical method to determine the relative height of a given point on the sample surface is as follows. The microscope objective is arranged to produce a spot on the object, which can be slightly de-focused. The distance of the illuminated spot on the object from the microscope objective then governs the size of the image produced on the CCD (i.e. the number of pixels illuminated by this image). The computer is programmed to determine the size of the image. As X-Y scanning takes place, the size of the image on the CCD will vary with the local height of the illuminated portion of the object, and can be determined by the computer. This makes a powerful analysis tool which can determine both the shape and contour and also the local composition of the object.

Another optical method to determine the relative height of a given point on the sample surface is to use confocal Raman spectroscopy techniques, for example as described above in relation to FIGS. 1–7, or using a conventional pinhole-type spatial filter. The height of the illuminated spot on the sample surface is determined as follows. The microscope objective lens 16 (FIGS. 1 or 4) is focused to a spot in the normal way, by movement of the lens 16 or of the sample 18 along the optical axis. For example, this can be done under the control of the computer 25, on a continuous basis as the spot is scanned in the X and Y directions across the sample surface, the computer continually servoing the focus so as to achieve maximum illumination of the pixels 42 (FIG. 2) or between the lines 44 (FIGS. 3 and 5). The movement required to achieve this is thus a measure of the height of the illuminated point on the sample surface, enabling the computer 25 to determine the height. Simultaneously, the computer also obtains the desired information about the concentration of the molecular species indicated by the selected Raman line, at the point concerned, by measuring the intensity of the maximum just obtained on the pixels 42,44. The height information and the Raman information are used as previously.

Topographical or profile or height information may also be obtained by the above confocal techniques in several other ways. For example, where the incident laser light is focused to a point, it may be scanned point by point over a full three dimensional volume of the sample. This gives depth information at each point within the scanned X-Y area of the sample. Alternatively, where a non-dispersive filter is used for the Raman analysis, and a two dimensional image is focused on the CCD, the focus may be adjusted to take a plurality of images, each representing a slice at a different depth within the volume of the sample. Three dimensional deconvolution algorithms are then used on the resulting data by the computer, in order to mathematically reconstruct data representing the Raman scattering at each point within the sample volume, reducing or removing the blurring referred to above.

Another use for the apparatus described is in the semiconductor manufacturing industry, to measure line widths of silicon and polymer photolithographic materials during masking and deposition processes. It is important to be able to determine the edges and sharpnesses of the polymer and silicon boundaries. The Raman analyser 20,124 can be tuned to pick up critical Raman lines for silicon and for the various polymers used. Images can be obtained over an area, and defects at edges with critical breakdowns can be detected. Also, when combined with the profile determination techniques discussed above, the heights of polymer depositions can be correlated with the image. This combination of Raman with edge profiling is useful to define the exact position of an edge to enable line widths to be determined. It can also be used to measure the width and depth of (say) a channel etched in a semiconductor substrate, such as gallium aluminium arsenide, and indicate the relative proportions of the gallium and the aluminium at the bottom of the channel, compared with those at the substrate surface.

We claim:

1. A spectroscopy method, comprising:

illuminating a sample to obtain therefrom a spectrum of scattered light;

analysing said spectrum;

passing at least one component of the analysed spectrum to a photodetector, light scattered from a given plane in the sample being brought to a tight focus in a given area on the photodetector while light scattered from other planes in the sample is brought to a more diffuse focus on the photodetector; and detecting light which is received in said given area on the photodetector, wherein the light received in said given area is detected without or separately from diffusely focused light outside said given area, thereby reducing the effect of light scattered from said other planes in the sample.

2. A method according to claim 1, wherein the photodetector comprises an array of pixels, and the light which is received in said given area is detected by selectively binning together the data from some of the pixels.

3. A method according to claim 1, wherein said step of detecting light in said given area on the photodetector provides confocal action in one dimension.

4. A method according to claim 3, wherein the light is passed through a one-dimensional spatial filter which provides confocal action in a second dimension.

5. A method according to claim 1, wherein the photodetector comprises a two-dimensional array of pixels, and the light which is received in said given area is detected by processing data representing an image received by said array.

6. A method according to claim 1, wherein said spectrum is a spectrum of Raman scattered light.

7. A method according to claim 1, including the step of obtaining topographical or surface profile data concerning the sample.

8. A method according to claim 1, in which the sample is illuminated at a focused spot.

9. A method according to claim 1, wherein the photodetector has a size corresponding to said given area.

10. A method according to claim 4, wherein said spatial filter comprises a slit.

11. Spectroscopy apparatus, comprising:

means for illuminating a sample to obtain therefrom a spectrum of scattered light;

means for analyzing said spectrum;

a photodetector;

means for passing at least one component of the analyzed spectrum to the photodetector, light scattered from a given plane in the sample being thereby brought to a tight focus in a given area on the photodetector while light scattered from other planes in the sample is brought to a more diffuse focus on the photodetector; and means for detecting light which is received in said given area on the photodetector, wherein said detecting means detects the light received in said given area without or separately from diffusely focused light outside said given area, thereby reducing the effect of light scattered from said other planes in the sample.

12. Apparatus according to claim 11, wherein the photodetector comprises an array of pixels.

13. Apparatus according to claim 12, including means for selectively binning together the data from some of the pixels.

14. Apparatus according to claim 12, wherein the photodetector comprises a two-dimensional array of pixels, and including computing means for receiving data from the array, representing an image received by the array, and for processing said image date to detect the light which is in said given area.

15. Apparatus according to claim 11, wherein said means for detecting light which is received in said given area on the photodetector provides confocal action in one dimension.

16. Apparatus according to claim 15, wherein a one-dimensional spatial filter is provided, through which the light is passed, the one-dimensional spatial filter providing confocal action in a second dimension.

17. Apparatus according to claim 11, wherein said spectrum is a spectrum of Raman scattered light.

18. Apparatus according to claim 11, including means for obtaining topographical or surface profile data concerning the sample.

19. Apparatus according to claim 11, in which the illuminating means is arranged to illuminate the sample at a focused spot.

20. Apparatus according to claim 11, wherein the photodetector has a size corresponding to said given area.

21. Apparatus according to claim 16, wherein said spatial filter comprises a slit.

* * * * *